(12) United States Patent
Herfert et al.

(10) Patent No.: US 8,371,475 B2
(45) Date of Patent: Feb. 12, 2013

(54) PROCESS FOR METERING SUPERABSORBENTS

(75) Inventors: Norbert Herfert, Altenstadt (DE); Herman Josef Feise, Kleinniedesheim (DE); Hanno Rüdiger Wolf, Heidelberg (DE)

(73) Assignee: BASF SE, Ludwigshafen (DE)

( * ) Notice: Subject to any disclaimer, the term of this patent is extended or adjusted under 35 U.S.C. 154(b) by 500 days.

(21) Appl. No.: 12/676,060

(22) PCT Filed: Sep. 12, 2008

(86) PCT No.: PCT/EP2008/062110
§ 371 (c)(1),
(2), (4) Date: Mar. 2, 2010

(87) PCT Pub. No.: WO2009/034153
PCT Pub. Date: Mar. 19, 2009

(65) Prior Publication Data
US 2010/0206897 A1    Aug. 19, 2010

Related U.S. Application Data

(60) Provisional application No. 60/971,636, filed on Sep. 12, 2007.

(51) Int. Cl.
*G01F 11/20*    (2006.01)
*G01F 11/00*    (2006.01)
*B67D 7/20*     (2010.01)
*B07B 13/00*    (2006.01)

(52) U.S. Cl. ................................ 222/1; 521/63; 536/87
(58) Field of Classification Search .................. None
See application file for complete search history.

(56) References Cited

U.S. PATENT DOCUMENTS

| | | | |
|---|---|---|---|
| 4,286,082 A * | 8/1981 | Tsubakimoto et al. | 526/240 |
| 4,646,510 A | 3/1987 | McIntyre | |
| 4,734,478 A | 3/1988 | Tsubakimoto et al. | |
| 4,927,346 A | 5/1990 | Kaiser et al. | |
| 5,102,585 A | 4/1992 | Pieper et al. | |
| 5,605,720 A | 2/1997 | Allen et al. | |
| 5,848,728 A | 12/1998 | Ricciardi et al. | |
| 6,033,199 A * | 3/2000 | Vonderhaar et al. | 425/81.1 |
| 6,300,275 B1 * | 10/2001 | Weir | 502/402 |
| 6,323,252 B1 * | 11/2001 | Gartner et al. | 521/149 |
| 7,451,666 B2 * | 11/2008 | Johanson | 73/866 |
| 2003/0130638 A1 * | 7/2003 | Baker | 604/368 |
| 2003/0136463 A1 * | 7/2003 | Zhou et al. | 141/129 |
| 2005/0090586 A1 * | 4/2005 | Kang et al. | 524/27 |
| 2006/0281871 A1 * | 12/2006 | Steffl | 525/426 |
| 2007/0100132 A1 * | 5/2007 | Neubauer et al. | 528/480 |
| 2010/0093949 A1 | 4/2010 | Herfert et al. | |

FOREIGN PATENT DOCUMENTS

| | | |
|---|---|---|
| JP | 08-134134 A | 5/1996 |
| WO | WO-6913335 A1 | 5/1996 |
| WO | WO-0033782 A1 | 6/2000 |
| WO | WO-03002164 A2 | 1/2003 |
| WO | WO-2007/003619 A1 | 1/2007 |
| WO | WO-2008055856 A1 | 5/2008 |
| WO | WO-2008055935 A2 | 5/2008 |

OTHER PUBLICATIONS

"SAP applikatoren Applikatoren für die Produktion von Wegwerf-Hygieneprodukten," Acrison International GmbH.
Graham, Andrew T., et al. Modern Superabsorbent Polymer Technology, "Commercial Processes for the Manufacture of Superabsorbent Polymers." New York: John Wiley & Sons, Inc., 1998, pp. 69-117.
Roberts, A.W., "Design and Performance Criteria for Screw Conveyors in Build Solids Operation," *Bulk Solids, Handling,*,Australia (2002), vol. 22., No. 6, pp. 436-444.
Ullmann's Encyclopedia of Industrial Chemistry: Sulfuric Acid and Sulfur Trioxide to Tetrahydrofuran, completely revised 6th edition, "Superabsorbents," vol. 35, pp. 73-93, Wiley-VCH, Weinheim 2003.
Bates, Lyn, "Ten Key Steps for Avoiding Screw Feeder Discharge Problems, "*Solids Handling,*, at http://www.ajax.co.uk/ScrewConPer.htm (last visited Jun. 22, 2007) or in Chemical Technology 2004 (1), 2004 pages 14-15.
International Search Report in PCT/EP2008/062110 dated Jan. 23, 2009.

* cited by examiner

*Primary Examiner* — Kevin P Shaver
*Assistant Examiner* — Christopher Bahr
(74) *Attorney, Agent, or Firm* — Marshall, Gerstein & Borun LLP

(57) ABSTRACT

Superabsorbents are metered by a process using a screw conveyor, wherein the superabsorbent is selected, or treated with a cohesion control agent, to have an unconfined yield strength of from 0.75 to 1.5 kPa at consolidation stress of 6 kPa.

11 Claims, No Drawings

PROCESS FOR METERING SUPERABSORBENTS

CROSS-REFERENCE TO RELATED APPLICATIONS

This is the U.S. national phase application of International Application No. PCT/EP2008/062110, filed Sep. 12, 2008, which claims the benefit of U.S. provisional application No. 60/971,636, filed Sep. 12, 2007, incorporated herein by reference in its entirety.

The present invention relates to a process for metering superabsorbents.

Superabsorbents are known. Superabsorbents are materials that are able to take up and retain several times their weight in water, possibly up to several hundred times their weight, even under moderate pressure. Absorbing capacity is usually lower for salt-containing solutions compared to distilled or otherwise de-ionised water. Typically, a superabsorbent has a centrifugal retention capacity ("CRC", method of measurement see hereinbelow) of at least 5 g/g, preferably at least 10 g/g and more preferably at least 15 g/g. Such materials are also commonly known by designations such as "high-swellability polymer", "hydrogel" (often even used for the dry form), "hydrogel-forming polymer", "water-absorbing polymer", "absorbent gel-forming material", "swellable resin", "water-absorbing resin" or the like. The materials in question are crosslinked hydrophilic polymers, in particular polymers formed from (co)polymerized hydrophilic monomers, graft (co)polymers of one or more hydrophilic monomers on a suitable grafting base, crosslinked ethers of cellulose or starch, crosslinked carboxymethylcellulose, partially crosslinked polyalkylene oxide or natural products that are swellable in aqueous fluids, examples being guar derivatives, of which water-absorbing polymers based on partially neutralized acrylic acid are most widely used. Superabsorbents are usually produced, stored, transported and processed in the form of dry powders of polymer particles, "dry" usually meaning less than 5 wt.-% water content. A superabsorbent transforms into a gel on taking up a liquid, specifically into a hydrogel when as usual taking up water. By far the most important field of use of superabsorbents is the absorbing of bodily fluids. Superabsorbents are used for example in hygiene products, examples of which are diapers for infants, incontinence products for adults or feminine hygiene products. Examples of other fields of use are as water-retaining agents in market gardening, as water stores for protection against fire, for liquid absorption in food packaging or, in general, for absorbing moisture.

Processes for producing superabsorbents are also known. The acrylate-based superabsorbents which dominate the market are produced by radical polymerization of acrylic acid in the presence of a crosslinking agent (the "internal crosslinker"), usually in the presence of water, the acrylic acid being neutralized to some degree in a neutralization step conducted prior to or after polymerization, or optionally partly prior to and partly after polymerization, usually by adding a alkali, most often an aqueous sodium hydroxide solution. This yields a polymer gel which is comminuted (depending on the type of reactor used, comminution may be conducted concurrently with polymerization) and dried. Usually, the dried powder thus produced (the "base polymer") is surface crosslinked (also termed surface "post"crosslinked) by adding further organic or polyvalent cationic crosslinkers to generate a surface layer which is crosslinked to a higher degree than the particle bulk. Most often, aluminium sulphate is being used as polyvalent cationic crosslinker. Applying polyvalent metal cations to superabsorbent particles is sometimes not regarded as surface crosslinking, but termed "surface complexing" or as another form of surface treatment, although it has the same effect of increasing the number of bonds between individual polymer strands at the particle surface and thus increases gel particle stiffness as organic surface crosslinkers have. Organic and polyvalent cation surface crosslinkers can be cumulatively applied, jointly or in any sequence.

Surface crosslinking leads to a higher crosslinking density close to the surface of each superabsorbent particle. This addresses the problem of "gel blocking", which means that, with earlier types of superabsorbents, a liquid insult will cause swelling of the outermost layer of particles of a bulk of superabsorbent particles into a practically continuous gel layer, which effectively blocks transport of further amounts of liquid (such as a second insult) to unused superabsorbent below the gel layer. While this is a desired effect in some applications of superabsorbents (for example sealing underwater cables), it leads to undesirable effects when occurring in personal hygiene products. Increasing the stiffness of individual gel particles by surface crosslinking leads to open channels between the individual gel particles within the gel layer and thus facilitates liquids transport through the gel layer. Although surface crosslinking decreases the CRC or other parameters describing the total absorption capacity of a superabsorbent sample, it may well increase the amount of liquid that can be absorbed by hygiene product containing a given amount of superabsorbent.

Other means of increasing the permeability (to be precise, the "gel bed permeability", "GBP" or the "saline flow conductivity", "SFC") of a superabsorbent are also known. These include admixing of superabsorbent with fibres such as fluff in a diaper core or admixing other components that increase gel stiffness or otherwise create open channels for liquid transportation in a gel layer. Usually, components increasing the GBP or SFC are referred to as permeability enhancing agents ("PEA").

One problem frequently associated with using additives to a superabsorbent is that free flow and forced feeding characteristics of the superabsorbent are impeded. This means that conveying superabsorbent, in particular forced feeding of superabsorbents, for instance forced feeding superabsorbent to a superabsorbent processing device such as a diaper-forming machine by a screw apparatus, may become difficult, or, in a design where product is not force-fed, but intended to flow freely from an elevated transport container such as a big bag into a feeding device such as a diaper machine's superabsorbent feed hopper located below the superabsorbent transport container, free flow may be impeded.

The problem of feeding is pronounced when it comes to metering. Metering out amounts of particulate material continuously and accurately is far more difficult than metering out fluids, and metering out superabsorbents which by nature are particulate solids is a critical step in diaper-forming, when a predetermined amount of superabsorbent is to be fed to that part of the diaper machine that produces the fluff and superabsorbent mixture to be included in an individual diaper. That predetermined amount of superabsorbent has to be metered out with accuracy and at high speed to support the high line speeds of diaper machines.

Frederic L. Buchholz and Andrew T. Graham (Hrsg.) in: "Modern Superabsorbent Polymer Technology", J. Wiley & Sons, New York, U.S.A./Wiley-VCH, Weinheim, Germany, 1997, ISBN 0-471-19411-5, give a comprehensive overview over superabsorbents and processes for producing superabsorbents. In its section on handling superabsorbents, this volume discloses that superabsorbents can be moved by equipment such as belt conveyors, bucket conveyors, screw conveyors, vibratory conveyors and dilute and dense-phase pneumatic conveyors, depending on plant layout and the results expected from the transport process. Pneumatic conveyors are preferred for longer distance transport whereas low-velocity mechanical conveyors are advantageous for shorter distances. A combination of particulate silica with polyols or polyalkylene glycols is disclosed as flow aid for polymers and copolymers of poly(acrylamide).

Ullmann's Encyclopedia of Industrial Chemistry, 6$^{th}$ Edition, Volume 35, Wiley-VCH, Weinheim 2003, (ISBN 3-527-30385-5), keyword "Superabsorbents" points out that fast running diaper machines and modern storage and conveying systems demand adjusted flowability.

A. W. Roberts, Bulk Solids Handling, 22 (2002) No. 6, 436-444, gives an overview of design and performance criteria for screw conveyors in bulk solids operation. It is pointed out that the performance of screw conveyors is particularly sensitive to variations in the flow properties of the bulk solids being conveyed and that determining the flow properties of the bulk solid is important. Lyn Bates lists "Ten Key Steps for Reliable Screw Conveyor Performance" at http://www.ajax.co.uk/ScrewConPer.htm (last visited 22$^{nd}$ Jun. 2007) or in Chemical Technology (2004) (1) 14-15.

US 2003/0 130 638 A1 discloses a part diaper-forming apparatus, which deposits superabsorbent on a fibrous substrate material. The apparatus comprises a feed tray and a shuttle pan which forms the feed tray's lower part. Superabsorbent is fed by means providing a relatively consistent and controllable flow of superabsorbent, such as a vibratory feeder or an auger screw.

U.S. Pat. No. 5,102,585 teaches a diaper-forming machine in which superabsorbent is discharged from a feeder by a means providing a selected mass flow rate such as a screw into a conveying gas stream for further processing, for example the LWF3-35 feeder manufactured by K-tron Corp. Pitman, N.J., U.S.A.

U.S. Pat. No. 5,605,720 relates to the application of hot melt adhesive to a diaper backsheet. In this process, a mixture of a particulate polymer adhesive and a tackifier is fed to an extruder and formed into a homogeneous melt, and continuously discharged. The solid components are metered into the extruder's feed hopper by suitable weigh feeding equipment. Preferably, the extruder is a twin-screw apparatus.

WO 00/33 782 A1 discloses an apparatus for forming a substantially uniform distribution of superabsorbent within a fibre web. Superabsorbent is metered into a delivery gas stream by a feeder which is suitable to deliver a selected mass flow rate of superabsorbent, for example the LWF3-35 feeder manufactured by K-tron Corp. Pitman, N.J., U.S.A.

WO 96/13 335 A1 relates to a method for forming a pulsed gas stream comprising superabsorbent particles. The superabsorbent is delivered as stream of metered particles by a screw feeder to a receiver of the particle accelerating part of the apparatus where they are picked up by the gas stream. The receiver comprises a particle storage chamber that assists in dispersing the particles and smoothes particle concentration variations.

U.S. Pat. No. 5,848,728 discloses a multi-flight notched metering auger screw provided to discharge a uniform flow of solid material.

The product brochure bearing the designation "SAP-01 de" from Acrison International GmbH, Wasserstraße/Bracht 3, 57334 Bad Laasphe, Germany, discloses basic, middle and highest level metering units for superabsorbents, either volumetric of gravimetric.

Japanese patent application publication no. 08-134 134 teaches the addition of a surfactant such as polyethylene glycol having an average molecular weight of 10 000 to 100 000 to superabsorbent gel and subsequent drying.

WO 03/002 164 A2, U.S. Pat. No. 4,286,082 and U.S. Pat. No. 4,734,478 repeat that additives such as surfactants or inert inorganic particles like silica are means to prevent superabsorbent agglomeration or facilitate rehydrating the superabsorbent.

WO 2007/003619 A1 discloses feeding additives, preferably superabsorbent fines, into a kneading reactor for producing superabsorbents, using a screw, preferably a self-cleaning double screw conveyor. It is recommended to use a screw long enough to achieve a steady flow. The screw is fed by a metering unit, for example a star feeder or a metering flap.

U.S. provisional patent application no, 60/858,260 (filed 10$^{th}$ Nov. 2006) relates to a superabsorbent having superior gel bed permeability and conveying properties, which is treated with a permeability enhancing agent and a cohesion control agent.

It is an object of the present invention to provide an improved superabsorbent conveying process, in particular an improved process for metering out superabsorbents accurately, uniformly and at high speed without pulsations. Further, the process should be capable of metering superabsorbent without further means supporting steady, non-pulsating flow such as residence chambers or dispersion in gas streams.

We have found that this object is achieved by a process for metering superabsorbents wherein the superabsorbent is metered using a screw conveyor and selected, or treated with a cohesion control agent, to have an unconfined yield strength of from 0.75 to 1.5 kPa at consolidation stress of 6 kPa.

According to this invention, metering, as opposed to mere conveying superabsorbents from one place to another, is a process of conveying definite amounts of superabsorbent. Metering comprises providing definite, pre-selected amounts of superabsorbents such as the amounts necessary to fill a container designed to contain defined volumes or weight amounts of superabsorbent for storage or transport, or the amount intended to be included in a certain number of superabsorbent-containing articles, for example one diaper or a certain number of diapers produced using a common, pre-metered stock of superabsorbent. Metering also comprises feeding or conveying superabsorbent at a pre-selected, controlled rate. Metering implies a certain accuracy of the metered amount or controlled rate that is generally higher, usually much higher than that required for simple conveying, where accuracy is not a serious issue, if it is an issue at all. In general, the accuracy of metering is such that the maximum standard deviation of the actual amount or rate from the desired amount or rate is at most 10%, preferably at most 8% and more preferably at most 5%. Lower values, such as at most 3% or at most 1% are even more preferred.

Metering superabsorbent thus requires a steady, uninterrupted flow of superabsorbent powder. The choice of a screw conveyor as metering device and of the unconfined yield strength range pursuant to the present invention provides for superior metering of superabsorbents.

Metering is usually performed by pre-setting a desired value of an amount to be metered out or a rate, determining deviations of this amount or rate and making appropriate adjustments. The amount or rate may be measured as weight amount or weight per time, respectively, or as volume amount or volume per time, respectively. A convenient system for metering is the "loss in weight" system, where the loss in weight of a vessel that serves as feeding unit for the screw is constantly monitored. Instruments for determining weight, volume, weight or weight loss per time or volume per time are known. Apparatus and methods for adjusting these parameters are also known. With screw conveyors, the most convenient method for adjustment is setting and adjusting the screw speed.

Screw conveyors are known. According to this invention, fully enclosed screws are preferred over U-shaped trough-type conveyer screws. The screw conveyors to be used in this invention can be single, double- or multiple screw conveyors. Single- or double screw conveyors are preferred.

Any desired flight depth realizable by those skilled in the art and gradient of the screw may be used. The flight depth and the gradient are preferably selected such that the superabsorbent metered with the screw does not run out of the screw in an uncontrolled manner, but rather can be metered out in a controlled amount by virtue of the rotation of the screw. For metering, it is preferred to use a screw design that leads to a screw channel that is filled fully, at least in the region of the discharging end of the screw. How to appropriately design screws in view of the properties of a given material to be conveyed is known in the art.

In a preferred embodiment, the ratio of length to diameter of the screw (L/D ratio) is from 10 to 20; the L/D ratio is preferably from 12 to 17.

In case of single screw conveyors, the pitch to diameter ratio is typically in the range of at least 0.3 to at most 2.

In case of double screw conveyors, self-cleaning double screw conveyors are preferred. Self-cleaning is achieved by virtue of the double screw intermeshing. Both lightly intermeshing and deeply intermeshing screws are suitable. The double screw may be designed either in co-rotating or counter-rotating form. The double screw is preferably co-rotating. The double screw may be designed in any desired flight ratio.

The screw may comprise a choke section, that means a section (typically two flights) with reduced pitch, to increase screw channel filling and improve conveying.

The screw is driven preferably with an electric motor and an infinitely variable transmission. The infinitely variable transmission allows any desired rotary speed of the screws to be achieved, as a result of which the amount of the superabsorbent metered out is adjustable exactly.

The screw may be designed as a hollow screw or as a solid screw. The advantage of a hollow screw is its lower weight in comparison to a solid screw and the possibility of controlling the temperature of the screw from inside; the advantage of a solid screw is its greater stability, especially the greater fracture resistance.

Moreover, the screw may have a one-piece design or be composed of a plurality of elements. The screw preferably has a one-piece design. Suitable materials for the screw are all highly alloyed austenitic steels, ferritic-austenitic duplex materials, nickel-based alloys and titanium. In the selection of the suitable material, it should be ensured that the material is stable toward the pH values of superabsorbents in the range from 3 to 10, preferably from 5 to 7. Preferred material for the screw are highly alloyed austenitic steels. One example of a generally suitable steel is St 1.4112.

Conveying and metering screws for superabsorbents are well-known and are also available on the market. Examples of advanced designs are the Al-BDF series or Al-105 series models available from Acrison, Inc., Moonachie, N.J. 07074, U.S.A. or the "SAP Applikator" metering units available from Acrison International GmbH, 57334 Bad Laasphe, Germany. Simpler designs are also suitable, particularly in cases where no very accurate metering at very high speed is required.

The unconfined yield strength, usually designated $f_c$, is a property of bulk solids such as powders that depends on the consolidation stress, usually designated sigma_1 or $\sigma_1$, applied to the powder. Both values are in units of pressure, typically kPa. The dimensionless ratio of a consolidation stress value to the corresponding unconfined yield strength value is generally referred to as "flowability", usually abbreviated to "FFC", and depends on the particular solid. A plot of unconfined yield strength $f_c$ versus the consolidation stress $\sigma_1$ is generally referred to as "flow function". In principle, the flow function is formed by all of the inverted FFC values of a solid. All of these values and functions depend largely on interparticle (or "cohesive") forces and their ratio with gravity or other moving forces. The unconfined yield strength, flow function and FFC value can conveniently be measured using shear testing of powder samples. In the context of this invention, these values are measured according to the ASTM Standard D 6773-02: "Standard Shear Test Method for bulk Solids using the Schulze Ring Shear Tester" (Book of Standards 04.09). Testing equipment, in particular the Schulze Ring Shear Tester used in unconfined yield strength determination according to the pertinent ASTM Standard D 6773-02: "Standard Shear Test Method for bulk Solids using the Schulze Ring Shear Tester" (Book of Standards 04.09) is available from Dr.-Ing. Dietmar Schulze Schüttgutmesstechnik, Am Forst 20, 38302 Wolfenbüttel, Germany, or Jenike & Johanson, Inc., 400 Business Park Drive, Tyngsboro, Mass. 01879-1077, U.S.A. It should be noted that in that ASTM standard, the consolidation stress $\sigma_1$ is referred to as "major principal stress of a yield locus", which is a synonymous, less common designation of this parameter. A flow function is depicted in FIG. 23 e) of that standard.

The unconfined yield strength $f_c$ of a superabsorbent according to this invention is generally at least 0.75 kPa, preferably at least 0.85 kPa, and generally not more than 1.5, preferably not more than 1.2 kPa, at a consolidation stress of 6 kPa. These values correspond to FFC values at this consolidation stress of generally at least 4, preferably at least 5 and generally not more than 8, preferably not more than 7. Another suitable FFC value at that sigma_1 value is for example 6.

The superabsorbent in the present invention is a superabsorbent capable of absorbing and retaining amounts of water equivalent to many times its own weight under a certain pressure. In general, it has a centrifugal retention capacity (CRC, method of measurement see hereinbelow) of at least 5 g/g, preferably at least 10 g/g and more preferably at least 15 g/g. The ability to absorb liquids under moderate pressure, commonly measured as "absorption under a load of 0.9 psi", in short "AUL0.9 psi" (method of measurement see hereinbelow) (0.9 psi equal 6205 Pascal, although pressure is generally expressed as psi=pound per square inch in the contect of AUL measurements), generally is at least 20 g/g, preferably at least 21 g/g and most preferably at least 22 g/g. Preferably, the superabsorbent is a crosslinked polymer based on partially neutralized acrylic acid, and more preferably it is surface postcrosslinked. A "superabsorbent" can also be a mixture of chemically different individual superabsorbents in that it is not so much the chemical composition which matters as the superabsorbing properties.

Superabsorbents and processes for producing superabsorbents, including surface-postcrosslinked superabsorbents, are known. Synthetic superabsorbents are obtained for example by polymerization of a monomer solution comprising a) at least one ethylenically unsaturated acid-functional monomer, b) at least one crosslinker, c) optionally one or more ethylenically and/or allylically unsaturated monomers copolymerizable with the monomer a), and d) optionally one or more water-soluble polymers onto which the monomers a), b) and if appropriate c) can be at least partly grafted.

Suitable monomers a) are for example ethylenically unsaturated carboxylic acids, such as acrylic acid, methacrylic acid, maleic acid, fumaric acid and itaconic acid, or derivatives thereof, such as acrylamide, methacrylamide, acrylic esters and methacrylic esters. Acrylic acid and methacrylic acid are particularly preferred monomers. Acrylic acid is most preferable.

The monomers a) and especially acrylic acid comprise preferably up to 0.025% by weight of a hydroquinone half ether. Preferred hydroquinone half ethers are hydroquinone monomethyl ether (MEHQ) and/or tocopherols.

Tocopherol refers to compounds of the following formula:

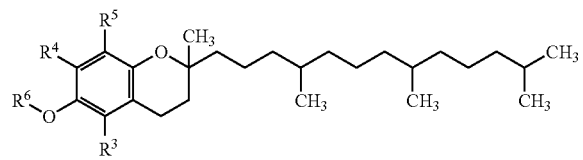

where $R^3$ is hydrogen or methyl, $R^4$ is hydrogen or methyl, $R^5$ is hydrogen or methyl and $R^4$ is hydrogen or an acid radical of 1 to 20 carbon atoms.

Preferred $R^6$ radicals are acetyl, ascorbyl, succinyl, nicotinyl and other physiologically tolerable carboxylic acids. The carboxylic acids can be mono-, di- or tricarboxylic acids.

Preference is given to alpha-tocopherol where $R^3=R^4=R^5$=methyl, especially racemic alpha-tocopherol. $R^6$ is more preferably hydrogen or acetyl. RRR-alpha-Tocopherol is preferred in particular.

The monomer solution comprises preferably not more than 130 weight ppm, more preferably not more than 70 weight ppm, preferably not less than 10 weight ppm, more preferably not less than 30 weight ppm and especially about 50 weight ppm of hydroquinone half ether, all based on acrylic acid, with acrylic acid salts being arithmetically counted as acrylic acid. For example, the monomer solution can be produced using an acrylic acid having an appropriate hydroquinone half ether content.

Crosslinkers b) are compounds having at least two polymerizable groups which can be free-radically interpolymerized into the polymer network. Useful crosslinkers b) include for example ethylene glycol dimethacrylate, diethylene glycol diacrylate, allyl methacrylate, trimethylolpropane triacrylate, triallylamine, tetraallyloxyethane as described in EP 530 438 A1, di- and triacrylates as described in EP 547 847 A1, EP 559 476 A1, EP 632 068 A1, WO 93/21237 A1, WO 03/104299 A1, WO 03/104300 A1, WO 03/104301 A1 and DE 103 31 450 A1, mixed acrylates which, as well as acrylate groups, comprise further ethylenically unsaturated groups, as described in DE 103 31 456 A1 and WO 04/013 064 A2, or crosslinker mixtures as described for example in DE 195 43 368 A1, DE 196 46 484 A1, WO 90/15830 A1 and WO 02/032962 A2.

Useful crosslinkers b) include in particular N,N'-methylenebisacrylamide and N,N'-methylenebismethacrylamide, esters of unsaturated mono- or polycarboxylic acids of polyols, such as diacrylate or triacrylate, for example butanediol diacrylate, butanediol dimethacrylate, ethylene glycol diacrylate, ethylene glycol dimethacrylate and also trimethylolpropane triacrylate and allyl compounds, such as allyl (meth)acrylate, triallyl cyanurate, diallyl maleate, polyallyl esters, tetraallyloxyethane, triallylamine, tetraallylethylenediamine, allyl esters of phosphoric acid and also vinylphosphonic acid derivatives as described for example in EP 343 427 A2. Useful crosslinkers b) further include pentaerythritol diallyl ether, pentaerythritol triallyl ether, pentaerythritol tetraallyl ether, polyethylene glycol diallyl ether, ethylene glycol diallyl ether, glycerol diallyl ether, glycerol triallyl ether, polyallyl ethers based on sorbitol, and also ethoxylated variants thereof. The process of the present invention may utilize di(meth)acrylates of polyethylene glycols, the polyethylene glycol used having a molecular weight between 300 and 1000.

However, particularly advantageous crosslinkers b) are di- and triacrylates of 3- to 15-tuply ethoxylated glycerol, of 3- to 15-tuply ethoxylated trimethylolpropane, of 3- to 15-tuply ethoxylated trimethylolethane, especially di- and triacrylates of 2- to 6-tuply ethoxylated glycerol or of 2- to 6-tuply ethoxylated trimethylolpropane, of 3-tuply propoxylated glycerol, of 3-tuply propoxylated trimethylolpropane, and also of 3-tuply mixedly ethoxylated or propoxylated glycerol, of 3-tuply mixedly ethoxylated or propoxylated trimethylolpropane, of 15-tuply ethoxylated glycerol, of 15-tuply ethoxylated trimethylolpropane, of 40-tuply ethoxylated glycerol, of 40-tuply ethoxylated trimethylolethane and also of 40-tuply ethoxylated trimethylolpropane.

Very particularly preferred for use as crosslinkers b) are diacrylated, dimethacrylated, triacrylated or trimethacrylated multiply ethoxylated and/or propoxylated glycerols as described for example in WO 03/104301 A1. Di- and/or triacrylates of 3- to 10-tuply ethoxylated glycerol are particularly advantageous. Very particular preference is given to di- or triacrylates of 1- to 5-tuply ethoxylated and/or propoxylated glycerol. The triacrylates of 3- to 5-tuply ethoxylated and/or propoxylated glycerol are most preferred. These are notable for particularly low residual contents (typically below 10 weight ppm) in the water-absorbing polymer and the aqueous extracts of the water-absorbing polymers produced therewith have an almost unchanged surface tension (typically at least 0.068 N/m) compared with water at the same temperature.

Examples of ethylenically unsaturated monomers c) which are copolymerizable with the monomers a) are acrylamide, methacrylamide, crotonamide, dimethylaminoethyl methacrylate, dimethylaminoethyl acrylate, dimethylaminopropyl acrylate, diethylaminopropyl acrylate, dimethylaminobutyl acrylate, dimethylaminoethyl methacrylate, diethylaminoethyl methacrylate, dimethylaminoneopentyl acrylate and dimethylaminoneopentyl methacrylate.

Useful water-soluble polymers d) include polyvinyl alcohol, polyvinylpyrrolidone, starch, starch derivatives, polyethyleneimines, polyglycols, polymers formally constructed wholly or partly of vinylamine monomers, such as partially or completely hydrolyzed polyvinylamide (so-called "polyvinylamine") or polyacrylic acids, preferably polyvinyl alcohol and starch.

The polymerization is optionally carried out in the presence of customary polymerization regulators. Suitable polymerization regulators are for example thio compounds, such as thioglycolic acid, mercapto alcohols, for example 2-mercaptoethanol, mercaptopropanol and mercaptobutanol, dodecyl mercaptan, formic acid, ammonia and amines, for example ethanolamine, diethanolamine, triethanolamine, triethylamine, morpholine and piperidine.

The monomers (a), (b) and optionally (c) are (co)polymerized with each other in the presence of the water-soluble polymers d), in 20% to 80%, preferably 20% to 50% and especially 30% to 45% by weight aqueous solution in the presence of polymerization initiators. Useful polymerization initiators include all compounds that disintegrate into free radicals under the polymerization conditions, examples being peroxides, hydroperoxides, hydrogen peroxide, persulfates, azo compounds and the so-called redox initiators. The use of water-soluble initiators is preferred. It is advantageous in some cases to use mixtures of various polymerization initiators, examples being mixtures of hydrogen peroxide and sodium or potassium peroxodisulfate. Mixtures of hydrogen peroxide and sodium peroxodisulfate can be used in any desired ratio. Suitable organic peroxides are for example acetylacetone peroxide, methyl ethyl ketone peroxide, tert-butyl hydroperoxide, cumene hydroperoxide, tert-amyl perpivalate, tert-butyl perpivalate, tert-butyl perneohexanoate, tert-butyl perisobutyrate, tert-butyl per-2-ethylhexanoate, tert-butyl perisononanoate, tert-butyl permaleate, tert-butyl perbenzoate, tert-butyl per-3,5,5-trimethylhexanoate and tert-amyl perneodecanoate. Further suitable polymerization initiators are azo initiators, for example 2,2'-azobis(2-amidinopropane) dihydrochloride, 2,2'-azobis(N,N-dimethylene)-isobutyramidine dihydrochloride, 2-(carbamoylazo)isobutyronitrile and 4,4'-azobis(4-cyanovaleric acid). The polymerization initiators mentioned are used in customary amounts, for example in amounts of from 0.01 to 5 mol %, preferably 0.1 to 2 mol %, based on the monomers to be polymerized.

The redox initiators comprise, as oxidizing component, at least one of the above-indicated per compounds and a reducing component, for example ascorbic acid, glucose, sorbose, ammonium bisulfite, ammonium sulfite, ammonium thiosulfate, ammonium hyposulfite, ammonium pyrosulfite, ammonium sulfide, alkali metal bisulfite, alkali metal sulfite, alkali metal thiosulfate, alkali metal hyposulfite, alkali metal pyrosulfite, alkali metal sulfide, metal salts, such as iron(II) ions or silver ions, sodium hydroxy-methylsulfoxylate, or sulfinic acid derivatives. The reducing component of the redox initiator is preferably ascorbic acid or sodium pyrosulfite. $1 \cdot 10^{-5}$ to 1 mol % of the reducing component of the redox initiator and $1 \cdot 10^{-5}$ to 5 mol % of the oxidizing component are used based on the amount of monomers used in the polymerization. Instead of the oxidizing component or in addition it is also possible to use one or more water-soluble azo initiators.

A redox initiator consisting of hydrogen peroxide, sodium peroxodisulfate and ascorbic acid is preferably used. These components are used for example in the concentrations of $1 \cdot 10^{-2}$ mol % of hydrogen peroxide, 0.084 mol % of sodium peroxodisulfate and $2.5 \cdot 10^{-3}$ mol % of ascorbic acid, based on the monomers.

It is also possible to initiate the polymerization by the numerous other known means to initiate polymerizations. On example is initiating polymerization by irradiating with radiation of sufficiently high energy, in particular ultraviolet light. Usually, when initiating polymerization by ultraviolet light, compounds are added which decompose into radicals upon irradiation by ultraviolet light. Examples of such compounds are 2-hydroxi-2-methyl-1-phenyl-1-propanone and/or alpha,-alpha-dimethoxi-alpha-phenylacetophenone.

The aqueous monomer solution may comprise the initiator in dissolved or dispersed form. However, the initiators may also be added to the polymerization reactor separately from the monomer solution.

The preferred polymerization inhibitors require dissolved oxygen for optimum effect. Therefore, the polymerization inhibitors can be freed of dissolved oxygen prior to polymerization, by inertization, i.e., by flowing an inert gas, preferably nitrogen, through them. This is accomplished by means of inert gas, which can be introduced concurrently, countercurrently or at entry angles in between. Good commixing can be achieved for example with nozzles, static or dynamic mixers or bubble columns. The oxygen content of the monomer solution is preferably lowered to less than 1 weight ppm and more preferably to less than 0.5 weight ppm prior to polymerization. The monomer solution is optionally passed through the reactor using an inert gas stream.

The preparation of a suitable polymer as well as further suitable hydrophilic ethylenically unsaturated monomers a) are described for example in DE 199 41 423 A1, EP 686 650 A1, WO 01/45758 A1 and WO 03/104300 A1.

Superabsorbents are typically obtained by addition polymerization of an aqueous monomer solution and optionally a subsequent comminution of the hydrogel. Suitable methods of making are described in the literature. Superabsorbents are obtained for example by gel polymerization in the batch process or tubular reactor and subsequent comminution in meat grinder, extruder or kneader, as described for example in EP 445 619 A2 and DE 198 46 413 A1;

polymerization in kneader with continuous comminution by contrarotatory stirring shafts for example, as described for example in WO 01/38402 A1;

polymerization on belt and subsequent comminution in meat grinder, extruder or kneader, as described for example in EP 955 086 A2, DE 38 25 366 A1 or U.S. Pat. No. 6,241,928;

emulsion polymerization, which produces bead polymers having a relatively narrow gel size distribution, as described for example in EP 457 660 A1;

in situ polymerization on a woven fabric layer which, usually in a continuous operation, has previously been sprayed with aqueous monomer solution and subsequently been subjected to a photopolymerization, as described for example in WO 02/94328 A2, WO 02/94329 A1.

The cited references are expressly incorporated herein for details of process operation. The reaction is preferably carried out in a kneader or on a belt reactor.

Continuous gel polymerization is the economically preferred and therefore currently customary way of manufacturing superabsorbents. The process of continuous gel polymerization is carried out by first producing a monomer mixture by admixing the acrylic acid solution with the neutralizing agent, optional comonomers and/or further auxiliary materials at different times and/or locations and then transferring the mixture into the reactor or preparing the mixture as an initial charge in the reactor. The initiator system is added last to start the polymerization. The ensuing continuous process of polymerization involves a reaction to form a polymeric gel, i.e., a polymer swollen in the polymerization solvent—typically water—to form a gel, and the polymeric gel is already comminuted in the course of a stirred polymerization. The polymeric gel is subsequently dried, if necessary, and also chipped ground and sieved and is transferred for further surface treatment.

The acid groups of the hydrogels obtained are partially neutralized in an acid neutralization step, generally to an extent of at least 25 mol %, preferably to an extent of at least 50 mol % and more preferably at least 60 mol % and generally to an extent of not more than 85 mol %, preferably not more than 80 mol %, and more preferably not more than 75 mol %.

Neutralization can also be carried out after polymerization, at the hydrogel stage. But it is also possible to carry out the neutralization to the desired degree of neutralization wholly or partly prior to polymerization. In the case of partial neutralization and prior to polymerization, generally at least 10 mol %, preferably at least 15 mol % and also generally not more than 40 mol %, preferably not more than 30 mol % and more preferably not more than 25 mol % of the acid groups in the monomers used are neutralized prior to polymerization by adding a portion of the neutralizing agent to the monomer solution. The desired final degree of neutralization is in this case only set toward the end or after the polymerization, preferably at the level of the hydrogel prior to its drying. The monomer solution is neutralized by admixing the neutralizing agent. The hydrogel can be mechanically comminuted in the course of the neutralization, for example by means of a meat grinder or comparable apparatus for comminuting gellike masses, in which case the neutralizing agent can be sprayed, sprinkled or poured on and then carefully mixed in. To this end, the gel mass obtained can be repeatedly meat-grindered for homogenization.

Neutralization of the monomer solution to the desired final degree of neutralization prior to polymerization by addition of the neutralizing agent or conducting the neutralization after polymerization is usually simpler than neutralization partly prior to and partly after polymerization and therefore is preferred.

The as-polymerized gels are optionally maintained for some time, for example for at least 30 minutes, preferably at least 60 minutes and more preferably at least 90 minutes and also generally not more than 12 hours, preferably for not more than 8 hours and more preferably for not more than 6 hours at a temperature of generally at least 50° C. and preferably at least 70° C. and also generally not more than 130° C. and preferably not more than 100° C., which further improves their properties in many cases.

The neutralized hydrogel is then dried with a belt or drum dryer until the residual moisture content is preferably below 15% by weight and especially below 10% by weight, the water content being determined by EDANA (European Disposables and Nonwovens Association) recommended test method No. 430.2-02 "Moisture content". The dry superabsorbent consequently contains up to 15% by weight of moisture and preferably not more than 10% by weight. The decisive criterion for classification as "dry" is in particular a sufficient flowability for handling as a powder, for example for pneumatic conveying, pack filling, sieving or other processing steps involved in solids processing technology. Optionally, however, drying can also be carried out using a fluidized bed dryer or a heated ploughshare mixer. To obtain particularly colourless products, it is advantageous to dry this gel by ensuring rapid removal of the evaporating water. To this end, dryer temperature must be optimized, air feed and removal has to be policed, and at all times sufficient venting has to be ensured. Drying is naturally all the more simple—and the product all the more colourless—when the solids content of the gel is as high as possible. The solvent fraction at addition polymerization is therefore set such that the solid content of the gel prior to drying is therefore generally at least 20% by weight, preferably at least 25% by weight and more preferably at least 30% by weight and also generally not more than 90% by weight, preferably not more than 85% by weight and more preferably not more than 80% by weight. It is particularly advantageous to vent the dryer with nitrogen or some other nonoxidizing inert gas. Optionally, however, simply just the partial pressure of oxygen can be lowered during drying to prevent oxidative yellowing processes. But in general adequate venting and removal of the water vapour will likewise still lead to an acceptable product. A very short drying time is generally advantageous with regard to colour and product quality.

The dried hydrogel (which is no longer a gel (even though often still called that) but a dry polymer having superabsorbing properties, which comes within the term "superabsorbent") is preferably ground and sieved, useful grinding apparatus typically including roll mills, pin mills, hammer mills, cutting mills or swing mills. The particle size of the sieved, dry hydrogel is preferably below 1000 µm, more preferably below 900 µm and most preferably below 850 µm and preferably above 80 µm, more preferably above 90 µm and most preferably above 100 µm.

Very particular preference is given to a particle size (sieve cut) in the range from 106 to 850 µm. Particle size is determined according to EDANA (European Disposables and Nonwovens Association) recommended test method No. 420.2-02 "Particle size distribution".

The dry superabsorbing polymers thus produced are typically known as "base polymers" and are then preferably surface postcrosslinked. Surface postcrosslinking can be accomplished in a conventional manner using dried, ground and classified polymeric particles. For surface postcrosslinking, compounds capable of reacting with the functional groups of the base polymer by crosslinking are applied, usually in the form of a solution, to the surface of the base polymer particles. Suitable postcrosslinking agents are for example:

- di- or polyepoxides, for example di- or polyglycidyl compounds such as phosphonic acid diglycidyl ether, ethylene glycol diglycidyl ether, bischlorohydrin ethers of polyalkylene glycols,
- alkoxysilyl compounds,
- polyaziridines, compounds comprising aziridine units and based on polyethers or substituted hydrocarbons, for example bis-N-aziridinomethane,
- polyamines or polyamidoamines and also their reaction products with epichlorohydrin,
- polyols such as ethylene glycol, 1,2-propanediol, 1,4-butanediol, glycerol, methyl-triglycol, polyethylene glycols having an average molecular weight Mw of 200-10 000, di- and polyglycerol, pentaerythritol, sorbitol, the ethoxylates of these polyols and also their esters with carboxylic acids or carbonic acid such as ethylene carbonate or propylene carbonate,
- carbonic acid derivatives such as urea, thiourea, guanidine, dicyandiamide, 2-oxazolidinone and its derivatives, bisoxazoline, polyoxazolines, di- and polyisocyanates,
- di- and poly-N-methylol compounds such as for example methylenebis(N-methylolmethacrylamide) or melamine-formaldehyde resins,
- compounds having two or more blocked isocyanate groups such as for example trimethylhexamethylene diisocyanate blocked with 2,2,3,6-tetramethylpiperidin-4-one.

If necessary, acidic catalysts can be added, examples being p-toluenesulfonic acid, phosphoric acid, boric acid or ammonium dihydrogenphosphate.

Particularly suitable postcrosslinking agents are di- or polyglycidyl compounds such as ethylene glycol diglycidyl ether, the reaction products of polyamidoamines with epichlorohydrin, 2-oxazolidinone and N-hydroxyethyl-2-oxazolidinone.

Surface postcrosslinking (often just "postcrosslinking") is typically carried out by spraying a solution of the surface postcrosslinker (often just "postcrosslinker") onto the hydrogel or the dry base polymer powder.

The solvent used for the surface postcrosslinker is a customary suitable solvent, examples being water, alcohols, DMF, DMSO and also mixtures thereof. Particular preference is given to water and water-alcohol mixtures, examples being water-methanol, water-1,2-propanediol, water-2-propanol and water-1,3-propanediol.

The spraying with a solution of the postcrosslinker is preferably carried out in mixers having moving mixing implements, such as screw mixers, paddle mixers, disk mixers, plowshare mixers and shovel mixers. Particular preference is given to vertical mixers and very particular preference to plowshare mixers and shovel mixers. Useful and known mixers include for example Lödige®, Bepex®, Nauta®, Processall® and Schugi® mixers. Very particular preference is given to high speed mixers, for example of the Schugi-Flexomix® or Turbolizer® type.

The spraying with the crosslinker solution can be optionally followed by a thermal treatment step, essentially to effect the surface-postcrosslinking reaction (yet usually just referred to as "drying"), preferably in a downstream heated mixer ("dryer") at a temperature of generally at least 50° C., preferably at least 80° C. and more preferably at least 80° C. and also generally not more than 300° C., preferably not more than 250° C. and more preferably not more than 200° C. The average residence time (i.e., the averaged residence time of the individual particles of superabsorbent) in the dryer of the superabsorbent to be treated is generally at least 1 minute, preferably at least 3 minutes and more preferably at least 5 minutes and also generally not more than 6 hours, preferably 2 hours and more preferably not more than 1 hour. As well as the actual drying taking place, not only any products of scissioning present but also solvent fractions are removed. Thermal drying is carried out in customary dryers such as tray dryers, rotary tube ovens or heatable screws, preferably in contact dryers. Preference is given to the use of dryers in which the product is agitated, i.e., heated mixers, more preferably shovel dryers and most preferably disk dryers. Bepex® dryers and Nara® dryers are suitable dryers for example. Fluidized bed dryers can also be used. But drying can also take place in the mixer itself, by heating the jacket or blowing a preheated gas such as air into it. But it is also possible for example to utilize an azeotropic distillation as a drying process. The crosslinking reaction can take place not only before but also during drying.

Preferably, the polymer is treated with a permeability enhancing agent, although this is not mandatory in the context of this invention. It is possible to treat the polymer simultaneously with surface crosslinker and permeability enhancing agent, but it is preferred to treat a surface-crosslinked polymer with a permeability enhancing agent.

The permeability agent can be any agent that increases gel bed permeability. It is preferably at least one permeability enhancing agent selected from the group formed by:
  particulate inorganic or organic solids;
  cationic polymers; and
  water-soluble polyvalent metal salts.

It is possible to apply more than one type of permeability enhancing agent. In general, the total amount of permeability enhancing agent added to a particular superabsorbent is adjusted to achieve the desired free swell GBP. Typically, permeability enhancing agents are used in an amount of at least 0.05 wt.-%, preferably at least 0.1 wt.-%, more preferably at least 0.3 wt.-% and generally at most 5 wt.-%, preferably at most 1.5 wt.-% and more preferably at most 1 wt.-%, in each case based on the total weight of the material.

Suitable particulate inorganic solids are superabsorbent permeability-enhancing particulate solids that are chemically inert with respect to a superabsorbent. Suitable permeability-enhancing particulate solids are well known in the art. Examples of suitable particulate inorganic solids include silicates and alumosilicates having a band, chain or sheet structure (such as montmorillonite, kaolinite, talc), zeolithes, silica, alumina, titanium dioxide, iron (II)oxide), magnesium carbonate, calcium carbonate, calcium phosphate, calcium sulphate and barium sulphate. Examples of suitable particulate organic solids include active carbon, superabsorbent fine particles such as undersized particles from sieving operations during superabsorbent production, cyclodextrines, cellulose and cellulose derivatives. Silica is preferred, in particular hydrophobic silica. The particle size of powders to be used as permeability enhancing agent is on a nanometer to micrometer scale. Preferably, the particle size is small enough as to yield a coating or partial coating of permeability enhancing agent on the superabsorbent particle surface. Generally, the particle size (measured as "d50", usually by laser diffraction, which means that 50% of the particles are smaller than the recorded value and 50% larger) is at least 0.1 micron, preferably at least 0.5 micron and more preferably at least 1 micron and generally at most 500 micron, preferably at most 200 micron and more preferably at most 100 micron. The individual powder particles of such substances are usually comprised of much smaller, so-called primary particles. A typical size of primary particles is on a nanometer scale. One example of a suitable particulate solid is hydrophobic silica having a d50 particle size of about 10 micron.

Particulate solid permeability enhancing agents may be applied by spraying a solution or dispersion thereof in water or an organic solvent onto the superabsorbent polymer powder while agitating and subsequent drying. It is also possible and preferred in case of insoluble or hydrophobic permeability enhancing agents to mix dry superabsorbent polymer powder and dry permeability enhancing agent.

Examples of suitable cationic polymers include polyalkenepolyamines, which are polymers formally constructed wholly or partly of vinylamine monomers, such as partially or completely hydrolyzed polyvinylamide (so-called "polyvinylamine") whose amine groups are always—even at very high pH values—partly present in a state of protonation to ammonium groups, cationic derivatives of polyacrylamides, polyethyleneimines, polyquaternary amines, for example condensation products of hexamethylenediamine, dimethylamine and epichlorohydrin, copolymers of hydroxyethylcellulose and diallyldimethylammonium chloride, copolymers of acrylamide and β-methacryloxyethyltrimethylammonium chloride, hydroxycellulose reacted with epichlorohydrin and then quaternized with trimethylamine, homopolymers of diallyldimethylammonium chloride or addition products of epichlorohydrin with amidoamines. Polyquaternary amines may further be synthesized by reaction of dimethyl sulfate with polymers, such as polyethyleneamines, copolymers of vinylpyrrolidone and dimethylaminoethyl methacrylate or copolymers of ethyl methacrylate and diethylaminoethyl methacrylate. Polyquaternary amines are available in a wide molecular range.

These permeability enhancing agents can also have the form of a crosslinked, cationic sheath, generated either by reacting reagents capable of forming a network, for example addition products of epichlorohydrin with polyamidoamines, or by applying cationic polymers capable of reacting with an added crosslinker, for example polyamines or polyimines combined with polyepoxides, multifunctional esters multifunctional acids or multifunctional (meth)acrylates. It is also possible to use any multifunctional amines having primary or secondary amino groups, for example polyethyleneimine, polyallylamine, polylysine, preferably polyvinylamine. Further examples of polyamines are ethylenediamine, diethylenetriamine, triethylenetetramine, tetraethylenepentamine, pentaethylenehexamine and polyethyleneimines and also polyamines having molar masses of up to 4 000 000 in each case.

Water-soluble polyvalent metal salts comprise bi- or more highly valent ("polyvalent") metal cations capable of reacting with the acid groups of the polymer to form complexes. Examples of polyvalent cations are or metal cations such as $Mg^{2+}$, $Ca^{2+}$, $Al^{3+}$, $Sc^{3+}$, $Ti^{4+}$, $Mn^{2+}$, $Fe^{2+/3+}$, $Co^{2+}$, $Ni^{2+}$, $Cu^{2+}$, $Zn^{2+}$, $Y^{3+}$, $Zr^{4+}$, $La^{3+}$, $Ce^{4+}$, $Hf^{4+}$, and $Au^{3+}$. Preferred metal cations are $Mg^{2+}$, $Ca^{2+}$, $Al^{3+}$, $Ti^{4+}$, $Zr^{4+}$ and $La^{3+}$, and particularly preferred metal cations are $Al^{3+}$, $Ti^{4+}$ and $Zr^{4+}$. The metal cations can be used not only alone but also in admixture with each other. Of the metal cations mentioned, any metal salt can be used that has sufficient solubility in the solvent to be used. Metal salts with weakly complexing anions such as for example chloride, nitrate and sulphate, hydrogen sulphate, carbonate, hydrogen carbonate, nitrate, phosphate, hydrogen phosphate, dihydrogen phosphate and carboxylate, such as acetate and lactate, are particularly suitable. It is particularly preferred to use aluminum sulfate.

The treatment of the superabsorbent polymer with solution of a polyvalent cation is carried out in the same way as that with surface postcrosslinker, including the selective drying step. Useful solvents for the metal salts include water, alcohols, DMF, DMSO and also mixtures thereof. Particular preference is given to water and water-alcohol mixtures such as for example water-methanol, water-1,2-propanediol, water-2-propanol and water-1,3-propanediol.

In a preferred embodiment, permeability is enhanced by applying aluminium(III), most preferably in the form of aluminium sulphate, and silica as the permeability enhancing agent.

In a preferred embodiment of the present invention, the permeability enhancing agent is applied to a superabsorbent that is surface crosslinked, or simultaneously with surface crosslinking, or partly simultaneously and partly after surface crosslinking. For example, a suitable method of applying a permeability enhancing agent is applying a polyvalent metal cation such as $Al^{3+}$ simultaneously with a surface crosslinker and applying a particulate solid such as silica after the step of surface crosslinking, for example during a cooling step conducted after drying the surface crosslinked product.

After any drying step, it is advantageous but not absolutely necessary to cool the product after drying. Cooling can be carried out continuously or discontinuously, conveniently by conveying the product continuously into a cooler downstream of the dryer. Any apparatus known for removing heat from pulverulent solids can be used, in particular any apparatus mentioned above as a drying apparatus, provided it is supplied not with a heating medium but with a cooling medium such as for example with cooling water, so that heat is not introduced into the superabsorbent via the walls and, depending on the design, also via the stirrer elements or other heat-exchanging surfaces, but removed from the superabsorbent. Preference is given to the use of coolers in which the product is agitated, i.e., cooled mixers, for example shovel coolers, disk coolers or paddle coolers, for example Nara® or Bepex® coolers. The superabsorbent can also be cooled in a fluidized bed by blowing a cooled gas such as cold air into it. The cooling conditions are set such that a superabsorbent having the temperature desired for further processing is obtained. Typically, the average residence time in the cooler will be in general at least 1 minute, preferably at least 3 minutes and more preferably at least 5 minutes and also in general not more than 6 hours, preferably 2 hours and more preferably not more than 1 hour, and cooling performance will be determined such that the product obtained has a temperature of generally at least 0° C., preferably at least 10° C. and more preferably at least 20° C. and also generally not more than 100° C., preferably not more than 80° C. and more preferably not more than 60° C.

The free swell gel bed permeability (free swell GBP) is an indicator of the ease of liquids transport through a layer of swollen superabsorbent, i.e. superabsorbent hydrogel. The test method for determining the free swell GBP is detailed below. The free swell GBP of the superabsorbent is generally at least 15 Darcies. Preferably, the free swell GBP is at least 20 Darcies and more preferably, it is at least 25 Darcies. Further examples of suitable free swell GPB values are values of at least 30 Darcies, at least 40 Darcies or at least 50 Darcies. There is no particular upper limit to this parameter in the context of this invention. The free swell GBP value can be increased by known means, in particular by adding more internal crosslinker, surface crosslinker, permeability enhancing agents or combinations thereof to almost any desired number. For contemporary applications, a free swell GBP of at most 200 Darcies will be sufficient in all but exceptional cases. A free swell GBP of at most 100 Darcies will be sufficient in most cases, and one of at most 60 Darcies will serve in most standard diaper applications.

According to this invention, the superabsorbent is selected to have an unconfined yield strength $f_c$ at consolidation stress sigma__1 of 6 kPa of at least 0.75 kPa and at most 1.5 kPa, or, in case it does not have an $f_c$ value in this range in its "as is" state, is treated with a cohesion control agent, to attain an $f_c$ value in that range.

Modern superabsorbents are generally treated with permeability enhancing agents. Since permeability enhancing agents tend to impede flowability of the superabsorbent powder in an "as is" state, that means without any flowability-modifying treatment after applying permeability enhancing agents and the last heat treatment step, the $f_c$ value of the superabsorbent in its "as is" state will be outside of this range in many, if not most cases.

In order to impart an $f_c$ value in the correct range to the superabsorbent, the superabsorbent is treated with a cohesion control agent. A cohesion control agent typically is a non-aqueous liquid having a viscosity of at least 20 mPas, preferably at least 30 mPas, more preferably at least 40 mPas and most preferably at least 80 mPas, and generally not more than 1 000 mPas, preferably not more than 700 mPas, all at 20° C.

A suitable cohesion control agent is at least one agent of this viscosity selected from the group formed by:
 alcohols
 poly glycols
 silicon oils
 hydrophilic modified silicon oils
 paraffin oils These cohesion control agents and methods of adding them to superabsorbent are known per se. Examples of suitable alcohols are 1,2-propylene glycol, 1,3-propane diol, 1,2-, 1,3- and 1,4-butandiol or glycerine. Examples of suitable polyglycols are poly ethylene glycols, poly propylene glycols or poly butylene glykols. Generally, these have a molecular mass of not more than 5 000 g/mol, preferably not more than 3 000 g/mol and more preferably not more than 2000 g/mol.

Preferred cohesion control agents are 1,2-propylene glycol, poly ethylene glycols with an average molecular weight of less than 1 500 g/mol, silicon oil, and hydrophilic modified silicon oil.

It is possible to apply more than one type of cohesion control agent. In general, the total amount of cohesion control agent added to a particular superabsorbent is adjusted to achieve the desired product properties, and to obtain a product that flows freely from a transport container such as a "big bag" into a feeding device. The optimum quantity of cohesion control agent depends on the type of superabsorbent and in particular on the type and amount of permeability enhancing agent. Typically, cohesion control agents are used in an amount of at least 100 wt.-ppm, preferably at least 200 wt.-ppm, more preferably at least 300 wt.-ppm and generally at most 5 000 wt.-ppm, preferably at most 3 000 wt.-ppm and more preferably at most 1 500 wt.-ppm, in each case based on the total weight of material.

The cohesion control agent is preferably applied to the polymer after surface crosslinking, and after the addition of permeability enhancing agent. Most preferably, the cohesion control agent is added after the heat treatment step applied during surface crosslinking or after a heat treatment step applied in the course of addition of permeability enhancing agent. It may be convenient to apply the cohesion control agent during a cooling step following surface crosslinking and addition of permeability enhancing agent, depending on whether the cooler provides sufficient mixing quality. It is always possible to add the cohesion control agent in a separate step, usually in a mixer, and preferably after surface crosslinking and adding a permeability enhancing agent. In some cases, it is possible to apply the cohesion control agent during surface crosslinking or addition of permeability enhancing agent, contingent upon inertness of the cohesion control agent during surface crosslinking.

Adding cohesion control agent usually necessitates no subsequent heating step. If a heating step should be necessary due to some special circumstances, care has to be taken to avoid any temperatures high enough for reaction between the cohesion control agent and the polymer.

Optionally, the superabsorbent is provided with further customary additives and auxiliary materials to influence storage or handling properties. Examples thereof are colorations, opaque additions to improve the visibility of swollen gel, which is desirable in some applications, surfactants or the like. Similarly, a final water content can be set for the superabsorbent, if desired, by adding water. These additives and auxiliary materials can each be added in separate processing steps, but one convenient method may be to add them to the superabsorbent in the cooler, for example by spraying the superabsorbent with a solution or adding them in finely divided solid or in liquid form, if this cooler provides sufficient mixing quality.

The surface-crosslinked superabsorbent is optionally ground and/or sieved in a conventional manner. Grinding is typically not necessary, but the sieving out of agglomerates which are formed or undersize is usually advisable to set the desired particle size distribution for the product. Agglomerates and undersize are either discarded or preferably returned into the process in a conventional manner and at a suitable point; agglomerates after comminution. The superabsorbent particle size is preferably not more than 1000 μm, more preferably not more than 900 μm, most preferably not more than 850 μm, and preferably at least 80 μm, more preferably at least 90 μm and most preferably at least 100 μm. Typical sieve cuts are for example 106 to 850 μm or 150 to 850 μm.

Superabsorbent metered by the process of the present invention can be used in any manner known for superabsorbents.

Superabsorbent Property Test Methods
Absorption Under Load 0.9 psi (AUL 0.9 psi)
The procedure for determining AUL 0.9 psi is disclosed in WO 00/62 825, pages 22-23 (referred to as "Absorbency Under Load" therein). A 317 gram weight is used to obtain the AUL 0.9 psi value.

Centrifuge Retention Capacity (CRC)
The method for determination of the Centrifuge Retention Capacity (CRC) is described in US patent application no. 2002/0165288 A1, paragraphs [0105] and [0106].

Flow Rate
Flow Rate is determined using EDANA (European Disposbles and Nonwovens Association, Avenue Eugène Plasky, 157, 1030 Brussels, Belgium, www.edana.org) Test Method 450.2-02 (available from EDANA).

Free Swell Gel Bed Permeability (Free Swell GBP)
The method for determination of the Free Swell Gel Bed Permeability (Free Swell GBP) is described in US patent application no. 2005/0 256 757 A1, paragraphs [0061] through [0075].

Unconfined Yield Strength ($f_c$)
The method for determining the unconfined yield strength ($f_c$) is described in ASTM Standard D 6773-02: "Standard Shear Test Method for bulk Solids using the Schulze Ring Shear Tester" (Book of Standards 04.09) (available from ASTM International, West Conshohocken, Pa., USA). The value is determined at a consolidation stress of 6 kPa. The FFC value at that consolidation stress is the ratio of that consolidation stress to the unconfined yield strength measured at that consolidation stress. In this ASTM standard, the consolidation strength is referred to as "major principal stress of a yield locus".

Mass Flow Rate
The mass flow rate test is designed to be indicative of the superabsorbent's conveying properties. A twin auger screw (pitch 48 mm, outer screw diameter 38.5 mm, inner screw diameter 15.5 mm, center-center screws distance 28.5 mm, screw-casing distance (clearing) 0.3 mm, length of screws 300 mm) equipped with an upstream hopper (40 liters volume, equipped with an agitator for avoiding product bridging) feeds into a receiving container placed on a scale. Superabsorbent is filled into the hopper and the twin screw operated at settings of 300 and 600 rpm. The amount of superabsorbent fed into the receiving container is continuously recorded.

EXAMPLES

Example 1

Polymer A (Comparative)

1040.00 g of glacial acrylic acid were added into a 4 liter glass reaction kettle equipped with a lid, thermocouple and nitrogen purge tube. Next, 3.12 g of pentaerythritol triallyl ether, 2430.17 g of de-ionised water, 3.83 g of Kymene® 736 (aqueous polyamidoamine epichlorohydrine adduct solution, obtained from Hercules Incorporated, Wilmington, Del., U.S.A.), and 500 g of ice made from deionized water were added. The monomer solution was then purged with nitrogen for 30 minutes. After 30 min, 11.44 g of 1 wt.-% aqueous hydrogen peroxide solution and 11.44 g of 1 wt.-% aqueous ascorbic acid solution were simultaneously added. After this initiation (the temperature rose rapidly and the monomer solution thickened), the purge tube was removed from the monomer solution and placed in the head space until the reaction temperature had peaked. The gel was kept overnight in an insulated container.

The gel was removed from the container and chopped once using a meat chopper (model 4812, manufactured by Hobart Corporation, Troy, Ohio, U.S.A.). 843.56 g of 50 wt.-% aqueous NaOH solution were added to the gel as evenly as possible. The gel was then kneaded thoroughly by hand and chopped twice using the Hobart meat chopper. Next, a solution of 10.40 g sodium metabisulfite in 200 g of deionized water was added to the gel as evenly as possible. The gel was again kneaded thoroughly by hand and chopped again twice using the Hobart meat chopper. The gel was then placed on a drum dryer (heated by steam, pressure >80 psi). The dried polymer flakes were collected and first crushed by hand, then milled using a pin mill (model ZM 200, manufactured by Retsch GmbH, Haan, Germany) at 14,000 rpm. The resulting powder was sifted to 850-160 micron using a sifter (model KS 1000, manufactured by Retsch GmbH, Haan, Germany) on setting 7 for ten minutes.

1 kg of the polymer powder was put into a mixer (laboratory ploughshare mixer model M 5, manufactured by Gebrüder Lödige Maschinenbau GmbH, Paderborn, Germany). A surface crosslinking solution was prepared by mixing 1.20 g of Denacol® EX 810 (ethylene glycol diglycidyl ether, obtained from Nagase ChemteX Corporation, Osaka, Japan), 20.00 g of propylene glycol, 20.00 g of deionized water, and 35.80 g of a 27 wt.-% aqueous aluminum sulfate solution into a beaker. At a mixer speed of 449 rpm, the surface crosslinker solution was added dropwise using a syringe to the polymer powder over a three minute time period. The mixer was then stopped, product sticking to the wall of the mixing vessel was scraped off (and re-united with the bulk), and mixing was continued for two more minutes at 449 rpm. The batch was then discharged into two stainless steel pans and placed in an oven at 120° C. for one hour. The pans the were removed from the oven and allowed to cool in a desiccator. The cooled product was then sifted, and the 850-150 micron cut designated Polymer A.

Example 2

Polymer B 1 kg of polymer A was placed in a stainless steel pan. Using a 3 ml syringe equipped with a needle, 2.0 g of polyethylene glycol 400 (polyethylene glycol of average molecular weight of 400 g/mol, "PEG-400") were added to the polymer, ensuring that the drops did not touch each other on the powder. The powder then was gently stirred with a spatula, carefully poured into a mixer (Lödige model M 5) and mixed for five minutes at 212 rpm to produce Polymer B.

Example 3

Polymer C

Polymer C was obtained following the procedure of Example 1, however, using the following amounts of chemicals:
1040.00 g of glacial acrylic acid
5.72 g of pentaerythritol triallyl ether,
2430.17 g of de-ionised water,
0.52 g of Kymene® 736
500 g of ice made from de-ionised water
11.44 g of 1 wt.-% aqueous hydrogen peroxide solution
11.44 g of 1 wt.-% aqueous ascorbic acid solution
843.56 g of 50 wt.-% aqueous NaOH solution
10.40 g sodium metabisulfite dissolved in 200 g of de-ionised water
1.50 g of Denacol® EX 810
13.00 g of propylene glycol
27.00 g of deionized water
no aqueous aluminum sulfate solution Example 4

Synthesis of Polymer D 92.4 g of acrylic acid, 0.022 g of pentaerythritol triallyl ether and 87.2 g of de-ionised water were mixed. 40.4 g of sodium carbonate were added, the temperature of the monomer solution was maintained below 30° C. during this neutralization reaction. Then, 0.081 g of 2,2'-azobisamidinopropane dihydrochloride and 0.054 g of hydrogen peroxide were mixed into the monomer mixture. The mixture was then heated to 62° C. and poured into a pan. 0.027 g of Brüggolit® FF6 (a sodium salt of a sulfinic acid derivative, obtained from L. Brüggemann KG, Heilbronn, Germany), dissolved in 5 g of de-ionised water, were added to initiate the polymerization. Due to the heat of polymerization the major part of the water evaporated during the reaction, and at the end a polymer mass with a residual moisture content of about 15 wt.-% was obtained. The polymer mass was dried in a drying oven at 120° C., milled and classified to a particle size distribution of 106-850 µm. The dry powder was blended with 0.25 wt.-% of hydrophobic silica (Sipernat® D-17 obtained from Degussa AG, Frankfurt, Germany) and then surface crosslinked by spraying a solution consisting of (wt.-% based on polymer powder) 0.46 wt.-% of Denacol® EX 810, 7.26 wt.-% of water and 2.29 wt.-% of 1,3-propandiol onto the particles and subsequent curing at 120° C. for one hour.

1 kg of this surface-crosslinked polymer was placed in a stainless steel pan. Using a 3 ml syringe equipped with a needle, 3.0 g of polyethylene glycol 400 (polyethylene glycol of average molecular weight of 400 g/mol, "PEG-400") were added to the polymer, ensuring that the drops did not touch each other on the powder. The powder then was gently stirred with a spatula, carefully poured into a mixer (Lödige model M 5) and mixed for five minutes at 212 rpm to produce Polymer D.

Polymer Properties

Properties of the polymers (CRC, AUL 0.9 psi ("AUL"), free swell GBP ("FSGBP"), Unconfined yield strength $f_c$ at a consolidation stress sigma_1 of 6 kPa, Flow Rate and Mass Flow Rate at 300 rpm ("MFR300") and at 600 rpm ("MFR600")) are summarized in Table 1.

TABLE 1

| Polymer | CRC [g/g] | AUL [g/g] | FSGBP [Darcies] | $f_c$ [kPa] | Flow Rate [g/s] | MFR300 [kg/h] | MFR600 [kg/h] |
| --- | --- | --- | --- | --- | --- | --- | --- |
| A | 27.8 | 19.1 | 129 | 0.21 | 11.7 | 709 | 1418 |
| B | 28.3 | 18.8 | 120 | 1.05 | 10.5 | 900 | 1782 |
| C | 31.7 | 22.8 | 13 | 1.09 | 11.4 | 896 | 1783 |
| D | 28.9 | 17.0 | 27 | 1.14 | no flow | 927 | 1782 |

The examples clearly demonstrate that the process of the present invention provides very efficient transport and metering of superabsorbents due to the steady and high flow of metered superabsorbent.

We claim:

1. A process for metering superabsorbents wherein a superabsorbent is metered using a screw conveyor and selected, or treated with a cohesion control agent, to have an unconfined yield strength of from 0.75 to 1.5 kPa at a consolidation stress of 6 kPa.

2. The process of claim 1, wherein a single screw is used.

3. The process of claim 1, wherein a double screw is used.

4. The process of claim 1, wherein the cohesion control agent is a non-aqueous liquid having a viscosity of at least 20 mPas and not more than 1,000 mPas at 20° C.

5. The process of claim 4, wherein the cohesion control agent is at least one agent selected from the group consisting of alcohols, polyglycols, silicon oils, hydrophilic modified silicon oils, and paraffin oils.

6. The process of claim 5, wherein the cohesion control agent is at least one agent selected from the group consisting of 1,2-propylene glycol, 1,3-propanediol, 1,2-butanediol, 1,3-butanediol, 1,4-butanediol, glycerine, polyethylene glycols, polypropylene glycols, polybutylene glycols, silicon oil, and hydrophilic modified silicon oil.

7. The process of claim 6, wherein the cohesion control agent is at least one agent selected from the group consisting of 1,2-propylene glycol, polyethylene glycols with an average molecular weight of less than 1 500 g/mol, silicon oil, and hydrophilic modified silicon oil.

8. The process of claim 4, wherein the cohesion control agent is used in an amount of at least 100 wt.-ppm and at most 5 000 wt.-ppm, based on the total weight of material.

9. The process of claim 5, wherein the cohesion control agent is used in an amount of at least 100 wt.-ppm and at most 5 000 wt.-ppm, based on total weight.

10. The process of claim 6, wherein the cohesion control agent is used in an amount of at least 100 wt.-ppm and at most 5 000 wt.-ppm, based on total weight.

11. The process of claim 7, wherein the cohesion control agent is used in an amount of at least 100 wt.-ppm and at most 5 000 wt.-ppm, based on total weight.

* * * * *